United States Patent
Smith et al.

(10) Patent No.: US 9,901,363 B2
(45) Date of Patent: Feb. 27, 2018

(54) RESECTION DEVICE AND RELATED METHODS OF USE

(71) Applicant: BOSTON SCIENTIFIC SCIMED, INC., Maple Grove, MN (US)

(72) Inventors: Paul Smith, Smithfield, RI (US); Samuel Raybin, Marlborough, MA (US); Naroun Suon, Lawrence, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 967 days.

(21) Appl. No.: 14/198,031

(22) Filed: Mar. 5, 2014

(65) Prior Publication Data

US 2014/0257321 A1    Sep. 11, 2014

Related U.S. Application Data

(60) Provisional application No. 61/776,502, filed on Mar. 11, 2013.

(51) Int. Cl.
*A61B 17/32* (2006.01)
*A61B 17/3205* (2006.01)
(Continued)

(52) U.S. Cl.
CPC .... *A61B 17/3205* (2013.01); *A61B 17/32056* (2013.01); *A61B 18/1492* (2013.01); *A61B 2017/00269* (2013.01); *A61B 2017/306* (2013.01); *A61B 2018/00291* (2013.01); *A61B 2018/00738* (2013.01); *A61B 2018/1407* (2013.01)

(58) Field of Classification Search
CPC .......... A61B 17/3205; A61B 17/32056; A61B 18/1492; A61B 2017/00269; A61B 2017/306; A61B 2018/00291
See application file for complete search history.

(56) References Cited

U.S. PATENT DOCUMENTS

| | | | |
|---|---|---|---|
| 6,306,081 | B1 | 10/2001 | Ishikawa et al. |
| 2002/0148475 | A1 | 10/2002 | Johnson et al. |

(Continued)

FOREIGN PATENT DOCUMENTS

| | | |
|---|---|---|
| EP | 1 518 507 A1 | 3/2005 |
| GB | 2365340 A | 2/2002 |

(Continued)

OTHER PUBLICATIONS

International Search Report for corresponding international application PCT/US2014/020791, dated May 9, 2014, 5 pages.

*Primary Examiner* — Ashley Fishback
(74) *Attorney, Agent, or Firm* — Bookoff McAndrews, PLLC (57) ABSTRACT

A tissue resection hood and related method of use for resecting the tissue are described. The tissue resection hood may include a distal end portion having an opening, a proximal end portion, and a cavity defined between the proximal and distal end portions, wherein the proximal end portion defines an opening configured to couple to an end of a sheath. The tissue resection hood may further include a cutting member configured to traverse the opening in the distal end portion and a mechanism configured to control a dimension of the cavity.

17 Claims, 9 Drawing Sheets

(51) Int. Cl.
  *A61B 17/00* (2006.01)
  *A61B 17/30* (2006.01)
  *A61B 18/00* (2006.01)
  *A61B 18/14* (2006.01)

(56) References Cited

U.S. PATENT DOCUMENTS

2005/0203489 A1    9/2005  Saadat et al.
2007/0255296 A1*  11/2007  Sauer ................. A61B 17/0057
                                                          606/144
2009/0228034 A1    9/2009  Sauer
2012/0204865 A1    8/2012  Filipi et al.

FOREIGN PATENT DOCUMENTS

JP       2005-192675       7/2005
JP       2006-334398      12/2006
WO    WO 2012/075409 A1    6/2012

* cited by examiner

RESECTION DEVICE AND RELATED METHODS OF USE

CROSS-REFERENCE TO RELATED APPLICATIONS

This application claims the benefit of priority from U.S. Provisional Application No. 61/776,502, filed on Mar. 11, 2013, the entirety of which is incorporated by reference herein.

FIELD

This disclosure relates generally to systems and methods for resecting tissue. More particularly, embodiments of the present disclosure relate to minimally-invasive systems for endoscopic mucosal resection.

BACKGROUND

Organ walls are composed of several layers: the mucosa (the surface layer), the submucosa, the muscularis (muscle layer), and the serosa. In gastrointestinal, colonic, and esophageal cancer, for example, small polyps or cancerous masses may form along the mucosa and often extend into the lumens of the organs. Conventionally, that condition is treated by cutting out a portion of the affected organ wall. This procedure, however, may cause extensive discomfort to patients, and poses health risks. Recently, physicians have adopted a minimally invasive technique called endoscopic mucosal resection (EMR), which removes targeted tissue, such as, e.g., the cancerous or abnormal tissues (polyps), while keeping the organ walls intact.

EMR may be performed with a suitable introduction sheath or an endoscope, which may be a long, narrow elongate member equipped with a light, video camera, and other instruments. During EMR, the endoscope may be passed down the throat or guided through the rectum, for example, to reach the target tissue. For certain procedures, a cutting device, such as a snare or wire loop, may be advanced through a endoscopic channel toward the target tissue. Once the cutting device is disposed adjacent the targeted tissue, the targeted tissue may be pulled towards the cutting device by, e.g., a vacuum suction, and the cutting device may resect the targeted tissue from surrounding tissue. Subsequently, the excised tissue may be extracted for examination, biopsy, or disposal.

In some cases, the tissue targeted for removal may be a polyp. Certain polyps, such as pedunculated polyps, are characterized by a stalk attached to the mucosal layer. Drawing such polyps into the cap without drawing in any other tissue is readily accomplished. Other polyps, such as sessile polyps, however, exhibit a broad base and they lay flat on the mucosal surface, devoid of a stalk. It is often difficult to grasp these polyps without drawing in a part of the muscularis layer.

The thickness of tissue varies at different locations within the body, and therefore, resecting appropriate depth of tissue is critical. EMR, as performed with conventional devices and methods, may resect excessive tissue, resulting in complications such as perforation, bleeding, and/or strictures. In some situations, the entire undesired tissue may not be removed. This situation may require additional procedures or result in the development of metastatic cancer, if the tissue left behind is diseased.

Therefore, there exists a need for an improved endoscopic mucosal resection tool that effectively resects undesired tissue from the body.

SUMMARY

Embodiments of the present disclosure relate to a tissue resection hood for resecting an undesired mass from a patient's body using a minimally invasive surgical system.

In accordance with an aspect of the present disclosure, a tissue resection hood may include a distal end portion having an opening, a proximal end portion, and a cavity defined between the proximal and distal end portions, wherein the proximal end portion defines an opening configured to couple to an end of a sheath. The tissue resection hood may further include a cutting member configured to traverse the opening in the distal end portion and a mechanism configured to control a dimension of the cavity.

Various embodiments of the tissue resection hood may include one or more of the following features: the dimension may be a volume of the cavity; the mechanism may be an adjustable structure disposed in the cavity; the mechanism may be configured to move relative to the opening of the distal end portion; the mechanism may be inflatable; the mechanism may be mechanically expandable; the opening in the distal portion may include at least one straight edge; the cutting member may be configured to traverse the opening in the distal end portion from a distal end to a proximal end; and a proximal end of the cavity may include stops configured to abut the cutting member.

In another embodiment, a medical device may include a sheath having a proximal end, a distal end, and a lumen extending therebetween. The medical device may further include a hood coupled to a distal portion of the sheath. The hood may include a distal end portion having an opening, a proximal end portion, and a cavity defined between the proximal and distal end portions, wherein the proximal end portion defines an opening configured to couple to the distal end of the sheath. The hood may further include a cutting member configured to traverse the opening in the distal end portion and a mechanism configured to adjust a dimension of the cavity.

Various embodiments of the medical device may include one or more of the following features: the mechanism may be an adjustable structure disposed in cavity; the mechanism may be configured to move relative to the opening; the mechanism may be inflatable; the opening in the distal portion may include at least one straight edge; the cutting member may be configured to transverse the opening from a distal end to a proximal end; a proximal end of the cavity may include stops configured to abut the cutting member.

In another embodiment, a method for resecting target tissue from a body may include advancing a medical device within a body lumen towards the target tissue. The medical device may include a sheath, and a hood coupled to a distal portion of the sheath. The hood may include a cavity having an opening. The hood may further include a cutting member configured to traverse the opening. The method may also include receiving target tissue within the cavity and activating the cutting member to move proximally relative to the opening.

Various embodiments of the present disclosure may include one or more of the following features: the mechanism may be an adjustable structure disposed in cavity; the cutting member may be configured to transverse the opening in the distal end portion from a distal end to a proximal end; a proximal end of the cavity includes stops configured to abut the cutting member; controlling an amount of target tissue received in the cavity by adjusting a position of a mechanism relative to the opening; and moving the cutting member across the opening from a distal end to a proximal end of the opening.

Additional objects and advantages of the present disclosure will be set forth in part in the description which follows, and in part will be obvious from the description, or may be learned by practice of the claimed invention. The objects and advantages of the claimed invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device in the patient.

Overview

Embodiments of the present disclosure relate to systems and methods for resecting tissue, including, e.g., cancerous or otherwise undesirable tissue from a patient's body. For example, the device may remove cancerous polyps or lesions from the mucosal walls of the colon, esophagus, stomach, or duodenum. A physician may also desire to resect tissue in order to conduct a biopsy or other examination.

In some embodiments, the resection device may include a hood assembly fitted on the distal end of any suitable introductory sheath, such as an endoscope, for facilitating the resection of tissue, such as, e.g., a polyp. The hood may be a hollow elongate member having an opening that defines a cavity for receiving the undesired tissue. The hood assembly may further include a volume control mechanism that adjusts the volume of the cavity to selectively adjust the volume of tissue drawn into the hood.

In addition, the hood assembly may include any suitable cutting tool known in the art. As discussed below, the cutting tool may be a cutting wire or snare. The cutting tool employed in the present disclosure may be flexible in nature and adapted to be moved across the opening of the cavity. The cutting tool may lie substantially parallel to the opening of the hood assembly. When the cutting tool is moved across the opening in, e.g., the proximal direction, the cutting tool will cut through any tissue disposed within the cavity of the hood assembly.

Exemplary Embodiments

Exemplary EMR Cap Assembly

Figure 1A:
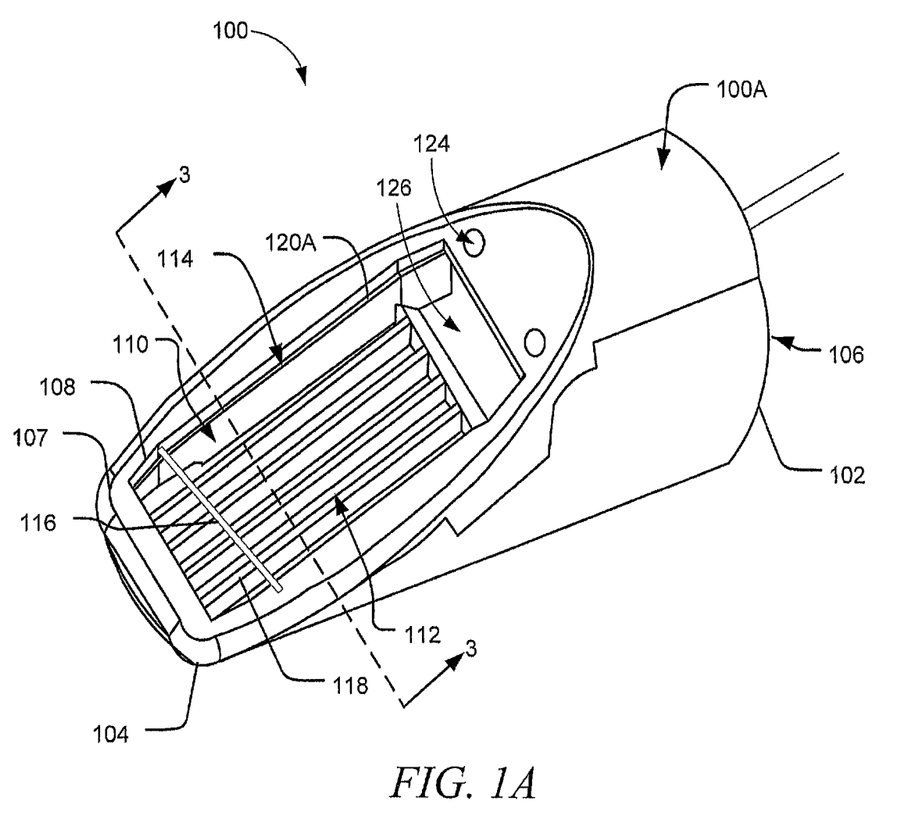
FIGS. 1A and 1B are views of a hood assembly according to an embodiment of the present disclosure.
Figure 1B:
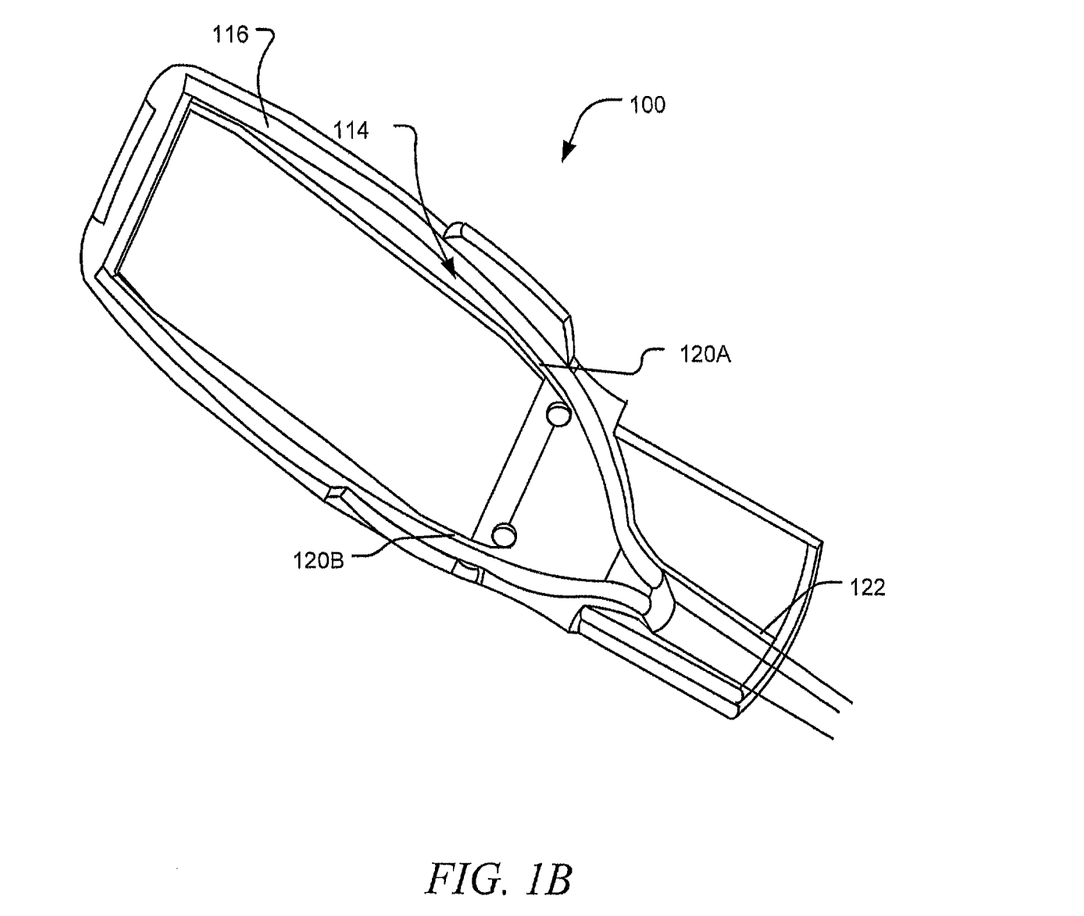

FIGS. 1A and 1B illustrate two views of a hood assembly 100 for resecting polyps, lesions, or otherwise unwanted tissue according to embodiments of the present disclosure. Particularly, FIG. 1A illustrates the hood assembly 100 and FIG. 1B illustrates the underside of component 100A of hood assembly 100. These figures will be commonly referenced to describe the structure and function of the hood assembly 100. The hood assembly 100 may be detachably connected to a distal end portion of any flexible or rigid introduction device or sheath, such as an endoscope used for colonoscopy, resectoscopy, or cholangioscopy. Alternatively, the hood assembly 100 may be configured to fit into and extend from a lumen of an introduction device or endoscope. Still further, hood assembly 100 may be integral with a distal end portion of a suitable introduction sheath.

Hood assembly 100 may be a generally hollow member having a proximal end 102, a distal end 104, and a lumen 106 extending between the proximal and distal ends 102, 104. A distal portion of the hood assembly 100 includes an opening 108 that, together with lumen 106 defines a cavity 110. The inner surface of the hood assembly 100 is connected to a volume control mechanism 112, which may be configured to selectively control the volume of the cavity 110.

Hood assembly 100 may include a substantially circular cross-section or it may have a cross-section similar to that of body cavities. Where required by given applications, hood assembly 100 may include elliptical, semi-circular, rhombic, or rectangular profiles. Moreover, the diameter of hood assembly 100 may vary based on the size of the body lumens in which it operates. For example, if hood assembly 100 is inserted through the urethra, its diameter may be relatively smaller. Conversely, if hood assembly 100 is inserted through the rectum, its diameter may be relatively larger. In addition, the dimensions of the hood assembly 100 may vary along its length. For example, a distal portion of hood assembly 100 may be tapered relative to a proximal end 102. In addition, the cross-sectional geometry of hood assembly 100 may vary along its length. For example, as shown in FIG. 1A, a proximal portion of hood assembly 100 may include a substantially circular cross-sectional geometry, while a distal portion of hood assembly may have a differing cross-sectional geometry.

Hood assembly 100 may be adapted to facilitate resection of tissue drawn into cavity 110. Cavity 110 may be defined by the opening 108 that may be at an angle to a longitudinal axis of the hood assembly 100. The slanted opening 108 provides for greater surface area contact between the hood assembly 100 and the targeted tissue. In addition, the slant angle of opening 108 may vary based on the organ or the procedure. For example, a narrower body organ, such as the esophagus, may call for an opening 108 slanted at a greater angle than for wider body organs, such as the stomach. In other embodiments, opening 108 may be substantially perpendicular to the longitudinal axis of the hood assembly, creating a distally facing opening. Still in further embodiments, opening 108 may be substantially parallel to a longitudinal axis of hood assembly 100. In such embodiments, opening 108 may extend from distal end 104 to proximal end 102 of hood assembly 100. In addition, those of ordinary skill will readily recognize that opening 108 may extend any suitable distance along the length of hood assembly 100.

The configuration of the opening 108 may vary, as desired. In the illustrated embodiment, the hood assembly 100 includes a substantially rectangular opening 108. The configuration of opening 108 may also depend on the cross-section of the hood assembly 100 or the slant angle of the distal end. For example, a square or rectangular shaped hood may define a rectangular opening. A cylindrical hood may define a circular or oval shaped opening. In addition, opening 108 may have one or more straight edges to, e.g., assist with tessellation of tissue, as will be discussed below in greater detail.

Any suitable material may be used to fabricate the hood assembly 100. For instance, rigid or semi-rigid materials such as metals (including super elastic materials such as Nitinol), polymers, resins, or plastics may be used. In some embodiments, a distal portion, e.g., distal end 104, of hood assembly 100 may be made of a flexible material while the remaining portion may be rigid. Alternatively, only the proximal end may be flexible. Flexible ends may allow the hood assembly 100 to form a seal with the contacting tissue and an endoscopic device. Further, a distal portion of hood assembly 100 may be configured to articulate relative to a proximal portion of hood assembly 100. Hood assembly 100 may also be optically clear, allowing physician to visualize tissue disposed within and/or around the hood assembly 100. Further, a biocompatible material that does not irritate the body lumens may be applied as a coating over the outer surface of hood assembly 100. The coating may also prevent blood from depositing and adhering to hood's surface. In addition, the coating may be a lubricious coating, which may help to facilitate insertion of hood assembly 100 into a patient's body.

In addition, outer surface of the hood assembly 100 may include markings. For example, radiopaque or sono-reflective markings (not shown) may be added to an exterior surface of the hood assembly 100. These markings facilitate detection of a position and/or orientation of the hood assembly 100 within the patient's body, and a surgeon, with the aid of suitable imaging equipment, may track the path followed by the endoscope system and avoid potential damage to sensitive tissues. In some embodiments, a portion or a substantial entirety of the periphery of opening 108 may include a radiopaque or sono-reflective marking.

The hood assembly 100 of the present disclosure provides two functionalities—a volume control mechanism for varying the volume of the tissue drawn into the hood and a cutting mechanism for cutting the drawn tissue. To this end, the hood assembly 100 may include a grate 112, made up of a number of longitudinal ridges 118. The ridges 118 extend from the inner surface of hood assembly 100 a given distance, and the plane defined by the upper surface of the ridges determines the depth to which tissue can be drawn into hood assembly 100, which in turn defines the volume of tissue to be resected. The hood assembly 100 further includes an integrated cutting tool 116, which may be employed to cut the tissue drawn within the grate 112. The following sections describe each of these elements in detail.

An interior of hood assembly 100 may include a suitable volume control mechanism, such as, e.g., grate 112. In certain instances, the volume control mechanism may include varying the size of opening 108. In some instances, the volume control mechanism may also include a surface having holes such that the holes may be configured to obtain the tissue. The person skilled in the art will appreciate that other suitable volume control mechanisms, such as, e.g., adjustable posts or the like may also be contemplated.

Grate 112 may include an area substantially similar to the area of the opening 108 such that the grate 112 may define a base for opening 108. In the illustrated embodiment, grate 112 includes multiple ridges 118 disposed in parallel spaced from each other, forming a grid-like structure. In addition, the ridges 118 run longitudinally within the hood assembly 100. It should be understood that the ridges 118 may assume any desired configuration. For example, the ridges may run transversely instead of longitudinally, or they may be slanted or angled within hood assembly 100. In other embodiments, the ridges 118 may include a combination of two or more of longitudinal, transverse, or slanted ridges.

As shown, each ridge 118 may be an elongate member having a rectangular cross-section. Other suitable cross-sections may include circular, triangular, irregular, or other suitable cross-sections known to those skilled in the art. The cross-sectional shape of ridges 118 may be uniform throughout their length. Alternatively, the cross-sectional shape may vary, as desired. In an alternate embodiment, the grate 112 may be a flat plate-like member that may form the base of the hood assembly 100.

Furthermore, grate 112 may lie parallel to the opening 108 of the hood assembly 100. In other embodiments, the grate 112 may be positioned at any angle to the opening 108. Ridges 118 may be made of suitable material, such as metal, polymer, or fiber.

Based on the tissue thickness, embodiments of the present disclosure may suitably select the configuration of the grate 112. In one embodiment, a uniform grate 112 may be selected. The uniform grate 112 may provide equal depth of the cavity 110 throughout its area. This configuration may result in non-uniform tissue depth resection, which may be undesirable in some situation. For example, the depth of tissue drawn into the hood assembly 100 near the edges of the opening 108 may be less that the tissue drawn in the center of opening 108.

To this end, in some embodiments of the present disclosure, a non-uniform depth of the tissue may be drawn within the grate 112. In general, the grate 112 may be designed such that the depth of the hood assembly 100 is greater around the edges than that at the center. For example, the ridges 118 may taper at the ends and thicken around the center portion. With such a configuration, the hood assembly 100 may receive a uniform depth of tissue across its opening 108. Alternatively, the grate 112 may be titled at an angle to vary the thickness of tissue drawn across its surface. It should be understood that depth pattern may vary based on the desired application and intended use.

In some embodiments, apart from the configuration of the grate 112, the position of the grate 112 may also determine the volume of the tissue drawn into the hood assembly 100. To control the volume of the cavity 110, the embodiments of the present disclosure allow adjustment in the position of the grate 112 within the hood assembly 100. Grate 112 may be moved as a whole to control the volume of tissue drawn. In some embodiments, the grate 112 may be held stationary and the ridges 118 may be adapted to move, controlling the volume of tissue drawn.

In an exemplary embodiment, the volume control mechanism may include an inflatable device (not shown), which may reduce the size of cavity 110 when inflated, thus decreasing the volume of the cavity 110. Alternatively, the device may be deflated to increase the volume of cavity 110 as required.

In general, grate 112 may move along an inner surface of the hood assembly 100 varying the hood's cavity size. Based on the desired thickness of tissue for resection, grate 112 may be selectively moved and secured at a desired position within the hood assembly 100. For example, grate 112 may move away or toward opening 108. The surface of the hood assembly 100 may include radiopaque or suitable markings that may assist in measuring the tissue thickness drawn into the hood assembly 100.

Various known mechanism may be used to vary the position of the grate 112. For example, grate 112 may be connected to pull wires to control the position. In one implementation, hood's inner surface may include projections or rails that may allow grate 112 to be fixed at varying positions. Alternatively, known span-fit connection, magnetic connections, or other known mechanism may also be contemplated. In some embodiments, pneumatic devices such as, e.g., pneumatic cylinder, pneumatic actuator, and other suitable devices known to those skilled in the art may be contemplated to vary the position of the grate 112. Still further, some embodiments of the present disclosure may include motor, such as, e.g., electric motor to vary position of the grate 112.

Apart from the grate 112, the depth adjustment mechanism may be embodied in a number of forms, all of which enable an operator to selectively control the volume of the cavity 110 based on the desired amount of tissue to be removed. For example, a limiting member (not shown) may be retractably introduced within the cavity of the hood assembly 100 from the proximal end. The position of the member may limit the size of opening 108, thereby limiting the volume of tissue drawn into the hood assembly 100. The limiting member may assume any desired shape including, but not limited to, a rod, a disc, a cuboid, or a selectively expandable cage-like structure. In each of the embodiments set out above, the axial position of the limiting member or the hood assembly 100 may be controlled using known retraction mechanisms. For example, a user may push or pull the limiting member or hood assembly 100 from its proximal end. In one embodiment, the limiting member may run on rails extending completely or partially along the length of hood assembly 100. The inner surface of the hood assembly 100 may include ridges or projections that may act as a ratchet to the limiting member. In addition, any suitable actuation means may be used to selectively extend and/or retract limiting member and/or hood assembly 100.

The hood assembly 100 may further include an integrated cutting tool 116 that is configured to resect tissue drawn into the hood assembly 100. The hood assembly 100 may include an underside component 110a, which may be configured to adapt a track 114. Track 114 may include a surface, which may allow movement of the cutting tool 116 along the opening 108, resecting the tissue. The component 110a of the hood assembly 100, as shown in FIG. 1B, illustrates the cutting tool 116 and the track 114 in detail.

In the illustrated embodiment, the track 114 includes elongate portions 120A, 120B diverging at an angle from a tail portion 122, forming a Y-shaped track. As shown, the elongate portions 120A, 120B diverge at similar angle from the tail portion 122. The divergence angle, however, may vary based on the dimensions of the opening 108. In general, elongate portions 120A, 120B may run along the sides of opening 108 of the hood assembly 100, and the tail portion 122 extends towards the proximal end of the hood assembly 100. As shown, the elongate portions 120A, 120B may have multiple bends along their lengths to form the two arms of the "Y". The bends or curves may be substantially smooth, allowing the operator to conveniently slide the cutting tool 116. In addition, the track 114 may be sufficiently wide to slidably receive a cutting tool 116.

Track 114 may be formed by cutting out a section of the thickness of the hood assembly 100, as shown in FIG. 1B. In one embodiment, track 114 may be configured as rails disposed on the underside of component 100A of hood assembly 100. Alternatively, the underside of component 100A of the hood assembly 100 may include support structures such as an edge, ridge, ledge, or projections that allow the cutting tool to rest parallel to the opening 108 of the hood assembly 100. In some embodiments, the support structures may include multiple equidistant protrusions extending along the length of the track 114. It will be understood that any other structure to maintain the cutting tool 116 within track 114 is conceivable and within the scope of the present disclosure.

Figure 2:
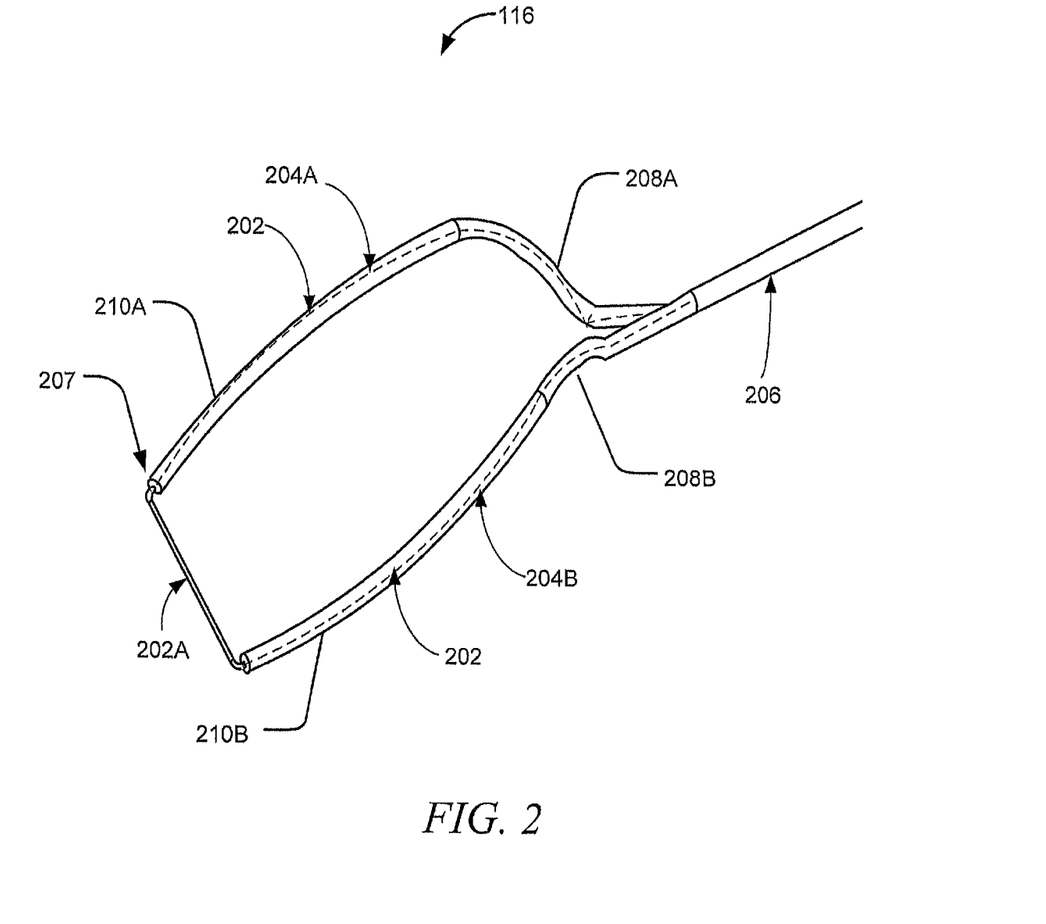
FIG. 2 illustrates a cutting tool according to embodiments of the present disclosure.

The cutting tool 116 is configured as a Y-shaped member that is adapted to traverse on the Y-shaped tract 114. FIG. 2 illustrates the cutting tool 116 in detail. In general, the cutting tool 116 includes a cutting wire 202, insulation arms 204A, 204B, and an actuation member 206 extending from a junction point of the insulation arms 204A, 204B. Here, each of the insulation arms 204A and 204B may include a lumen (not shown) such as the cutting wire 202 may advance through to configure as a loop 207. In general, the cutting tool 116 may configure as a loop 207 and the actuation member 206 may extend from the loop 207. Proximal ends of insulation arms 204A, 204B are connected to each other and cutting wire 202 extends between the distal tips of the insulation arms 204A, 204B, forming the loop 207. In addition, the insulation arms 204A, 204B diverge at an angle from a distal end of the actuation member 206 such that the insulation arms 204A, 204B along with the actuation member 206 form a Y-shapes cutting device. The elements of the cutting tool 116 may be made of a suitable flexible material allowing the tool to follow the contours of the track 114.

Cutting wire 202 can be held taut between the distal ends of the arms 204A, 204B such that when the cutting tool 116 advances on the track 114, the wire 202 traverses across the opening 108 and resects the tissue drawn into the hood assembly 100. The effective length of the cutting wire 202 can be relatively long or short, depending on the width of the opening 108. In general, the cutting wire 202 covers the width of opening 108 to resect the entire tissue drawn into the hood assembly 100. In an embodiment, cutting wire 202 may be an electrocautery wire.

Figure 3:
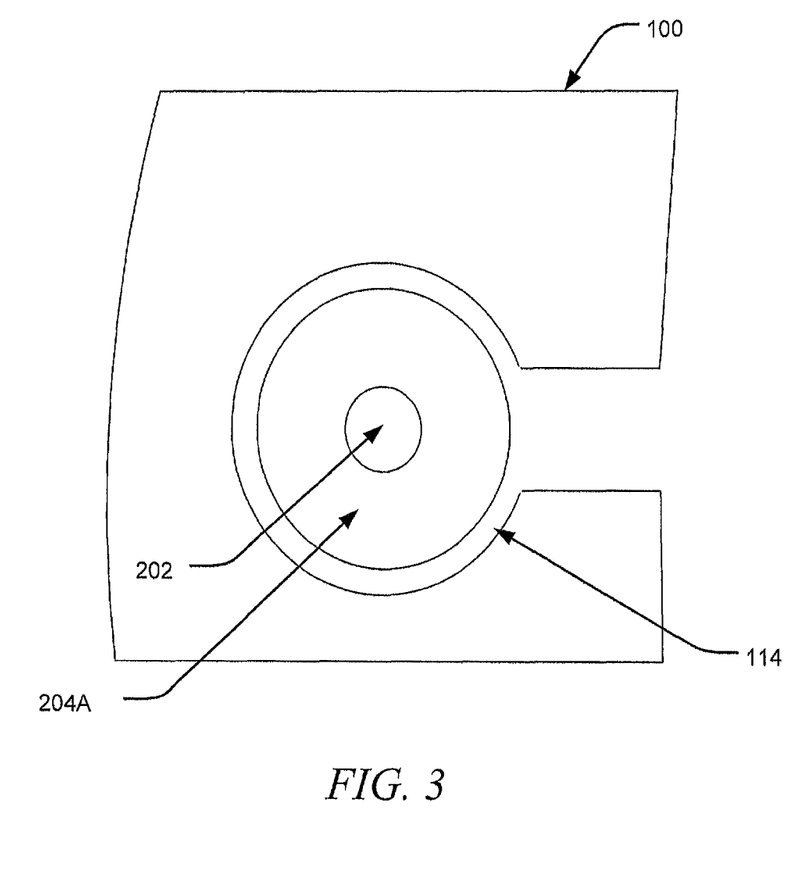
FIG. 3 illustrates a cross-sectional view of the hood assembly along line 3-3 shown in FIG. 1.

As shown, arms 204A, 204B may be elongate members having substantially circular cross-section. The cross-sectional configuration may vary, as desired, however. In general, the cutting wire 202 is configured as the loop 207 with an exposed section and the remaining sections converging towards the actuation member 206 are covered with suitable insulation material, forming insulation arms 204A, 204B. A cross-sectional view of the hood assembly 100 taken along line 3-3 in FIG. 1, shown in FIG. 3, illustrates the configuration of the actuation arms 204A, 204B. As shown, track 114 is carved within the thickness of the hood assembly 100.

In some embodiments, arms 204A, 204B may be hollow members allowing passage of cutting wire. In such configuration, the two ends of the cutting wire may run along the length of the arms 204A, 204B up to the actuation member 206. In some implementations, the cutting wire may remain within the one of the hollow arms 204A, 204B and actuation member 206 may expose the cutting wire 202 when required.

In an alternate embodiment, the cutting wire 202 may only extend between the distal tips of the insulation arms 204A, 204B. In such embodiments, the insulation arms 204A, 204B may include conductive wires that supplies required actuation energy to the cutting wire 202.

Arms 204A, 204B include angular proximal portions 208A, 208B diverging from the actuation member 206 at similar angle. In some embodiments, portions 208A, 208B may diverge at different angles to form an asymmetrical Y-shaped member. In addition, distal portions 210A, 210B of the arms 204A, 204B may be substantially straight sections running substantially parallel to each other. As shown, the proximal angular portions 208A, 208B and distal portions 210A, 210B may lie at an angle to each other. In one embodiment, proximal end portions may lie in a plane roughly perpendicular to the remainder of the arms 204A, 204B. In one embodiment of the present disclosure, length of arms 204A and 204B may vary. For instance, the length of arm 204A may be greater than the length of arm 204B, which may include cutting wire 202 extending at an angle across the opening 108.

In general, the distal portions 210A, 210B are dimensioned such that they extend in the elongate portions 120A, 120B of the track 114, while a portion of the proximal portions 208A, 208B and the actuation member 206 traverses on the tail portion 122. The angle of divergence of the proximal portions 208A, 208B may allow the distal portions 210A, 210B to align with the elongate portions 120A, 120B. Each arm 204A, 204B may be formed of multiple bends; angle and direction of each bend may be varied selectively. For example, the proximal portion 208A, 208B may also have multiple bends along its length based on the dimensions of the track.

Arms 204A, 204B may be made of any suitable insulative material that protects the hood's surface from electrical energy of the cutting wire. In addition, arms 204A, 204B may be made of flexible material that may deform based on the contours of track 114 during insertion and retraction. Arms 204A, 204B may also include any suitable coating or covering. For example, the outer surface may include a layer of lubricous material to facilitate convenient sliding over the track 114. Suitable material, including, e.g., Teflon, may be utilized for this purpose. Other material compositions may also be contemplated.

Actuation member 206 may be an elongate member, having, e.g., substantially circular cross-section, adapted to slide on the tail section 122 of the track 114. Actuation member 206 may run at least along the length of the hood assembly 100. In some embodiments, the actuation may run along the length of the associated introduction device connected to the proximal end of the hood assembly 100. In each of the embodiment, the actuation member may act as a means to push or pull the cutting tool 116 for resection. In addition, actuation member 206 may include a control mechanism for activating the cutting wire. For example, actuation member 206 may supply required electrical current to electrocautery wire 202. In addition, the actuation member 206 may be adapted to pull the cutting wire 202 through the arms 204A, 204B, thus exposing a clean section of cutting wire for subsequent electrocautery procedures.

In implementations where actuation member 206 extends up to the proximal end of the introduction device, the proximal end of the actuation member 206 may include a handle (not shown) for convenient actuation. The handle may also include the control mechanism for actuating the cutting wire 202. Alternatively, actuation member 206 may be connected to suitable retraction mechanism such as pull wires that extend up to the proximal end of the endoscopic device for pulling or pushing the cutting tool 116. In such configurations, the proximal end of the introduction device may include the control mechanism to actuate the cutting wire 202 and this control mechanism may be connected to the actuation arm using known mechanism such as conductive wires.

For effective tissue resection, the hood assembly 100 may also include additional geometrical features. The hood assembly 100 may include a lip 107 and stops 124 at the distal and proximal ends of opening 108, respectively which ensure the complete resection of the tissue drawn within the hood assembly 100. The lip 107 is located distal of opening 108, and stops 124, so that the cutting wire 202 completely traverses opening 108. In addition, the proximal edges of the opening include one or more wire stops 124 that limit the proximal movement of the cutting wire 202. Further, the stops 124 are made of heat-resistance material, such as PEEK, ceramic, or Teflon, that protects the hood assembly 100 from heated cutting wire 202.

In addition, the Portion of the hood assembly 100 proximate the proximal edge of the opening includes an opening 126 for receiving the cutting wire and the resected tissue. During resection, when the cutting tool is pulled proximally it moves into this opening and under lip 107. Further, the tissue resected during the movement of the cutting tool may be collected in this opening for removal from the patient's body. In an embodiment, this opening may be further connected to a suction source or other retrieval device, such as graspers, baskets, etc., for retrieving the resected tissue. Alternatively, the opening may be connected to a coagulation or vaporization source for reducing the tissue.

Different alternatives of the hood assembly 100 may be contemplated. For example, the cutting wire and insulation arms may include mechanism to visualize the position of the cutting tool during use. To this end, the cutting tool may be include radiopaque markings, coated with bright colors, or may be patterned suitably. Alternate visual indicators may also be connected to the cutting tool, as desired. The following sections describe some alternate hood assembly configurations.

Figure 4:
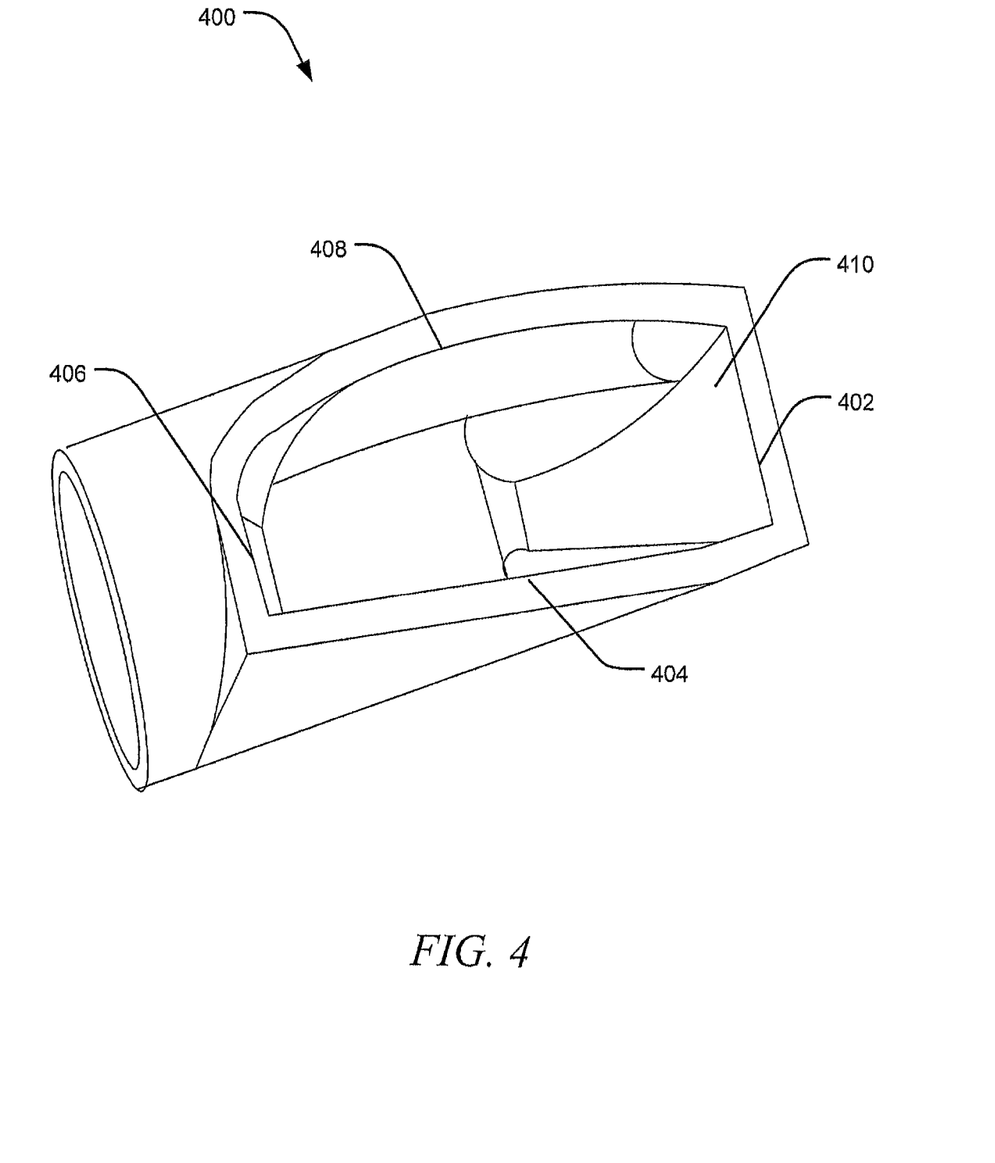
FIG. 4 illustrates an embodiment of a hood assembly having a modified opening, according to a further embodiment of the present disclosure.

FIG. 4 illustrates an exemplary hood assembly 400 that is similar in design and functionality to the hood assembly 100, but the opening 410 of the hood assembly 400 is patterned differently. As shown, the opening includes three substantially straight sides or edges 402, 404, and 406, while the fourth edge 408 may be curved. Where required by given applications, the cross-sectional shape of the opening 410 may be square, rhombic, hexagonal, triangular, semi-circular, quarter circle, or any desired shape having at least one edge with a straight portion.

In use, a cutting tool dissects the tissue drawn in the hood assembly 400 according to the cross-sectional shape of the opening 410. Here, the cutting tool 116 resects a tissue with three straight edges. Subsequent tissue resection may be accomplished by aligning one of the straight sides of the opening with a straight edge of the resected portion and repeating the process to remove the remaining portions of the lesion. Adjacent tissue sections may be continually removed in this manner without leaving undesired tissue behind.

In some embodiments, the outer surface of the hood assembly 400 or 100 may include visual indicators that may assist in alignment of the hood with the straight side of the resected tissue. Suitable visual indicators may include radiopaque markings, flags, or other known indicators that may be visualized through endoscopic optics.

Figure 5A:
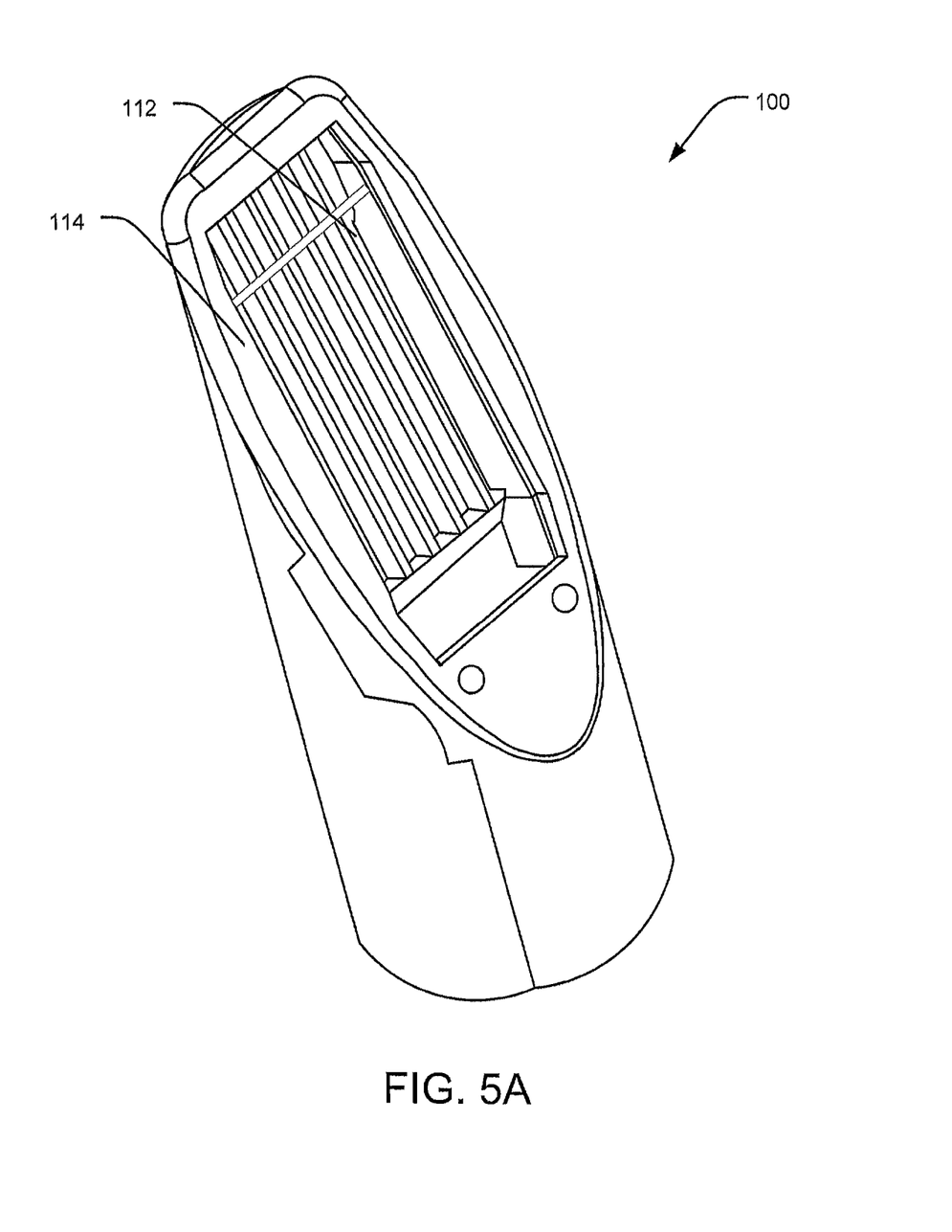
FIGS. 5A and 5B illustrate components of an embodiment of a hood assembly.
Figure 5B:
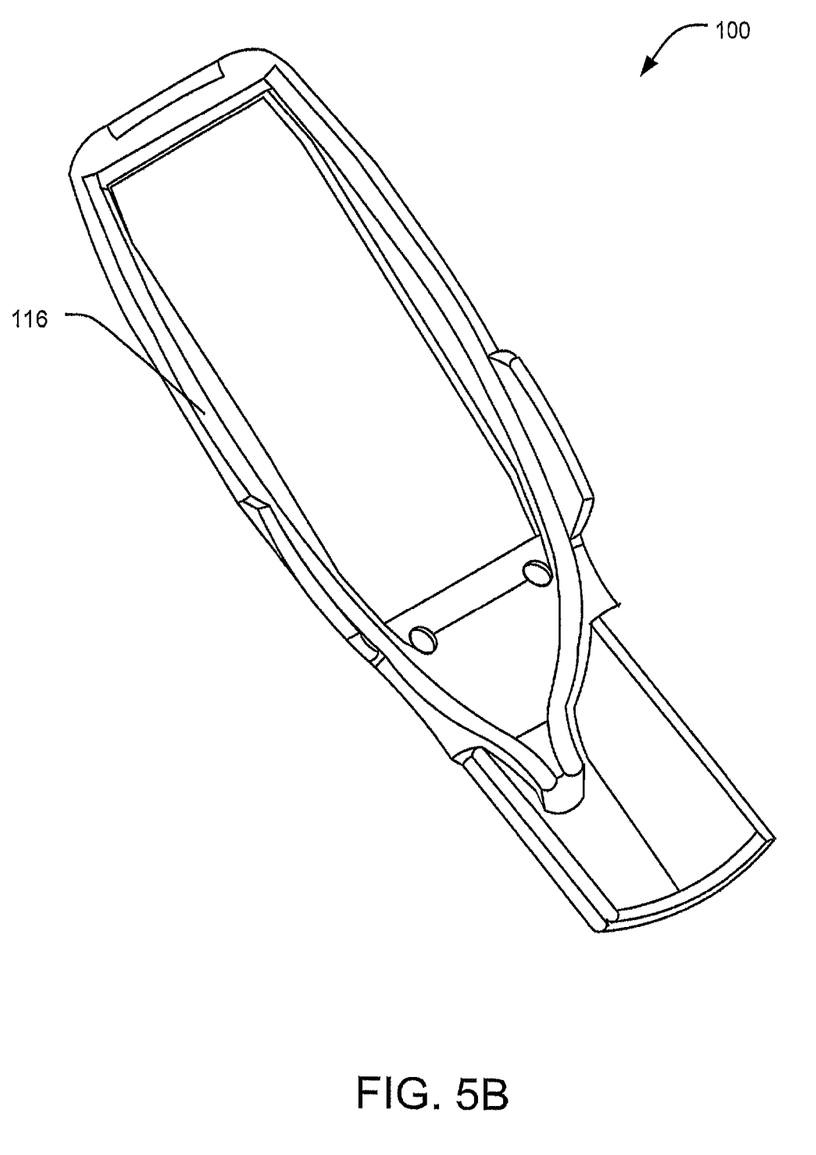

In another embodiment of the present disclosure, the hood assembly 100 may be split into two or more sections along a central axis. FIGS. 5A and 5B illustrate two sections of the hood assembly 100. In particular, FIG. 5A illustrates the lower section of the hood assembly 100 that includes the grate 112 and the track 114, while FIG. 5B illustrates the top section that includes the cutting tool 116. In addition, the track 114 may also be present on the underside of component 100A of the hood assembly (as shown in FIG. 1B). Although the illustrated embodiment depict two sections of the hood assembly, it should be understood that the hood assembly 100 may be split into multiple sections, as desired.

The sections of the hood assembly 100 may be assembled by a user conveniently. In some cases, the assembly may even occur inside of the body. Splitting the hood assembly 100 and assembling it later may be useful in situations where the surgeon may decide to change the grate 112 disposed within the hood assembly 100 for varying the resection depth. As the dimensions of grate 112 may be greater that the diameter of the hood assembly 100 and that of the working channel of the endoscopic device, insertion and retraction of the grate 112 may be convenient by disassembling the sections of the hood assembly 100.

The hood assembly 100 may be assembled onto the distal end of the endoscopic device by known connection mechanisms. For example, a second introduction sheath may be used to accomplish this. Once the hood sections are delivered to the distal end of the endoscope by, e.g., another introduction sheath, the multiple parts of the hood may be assembled together onto the distal end of the endoscope.

In certain instances, dimensions of the hood assembly 100 may be larger than the dimensions of the working channel of the endoscope. Here, splitting the hood assembly 100 may allow disassembling the hood assembly 100 and assembling it onto the distal end of the endoscope when required. In addition, the user may advance the cutting wire 202 through the working channel and may assemble the wire 202 with the hood assembly 100 by closing the hood assembly 100.

Exemplary Resection Device

Figure 6:
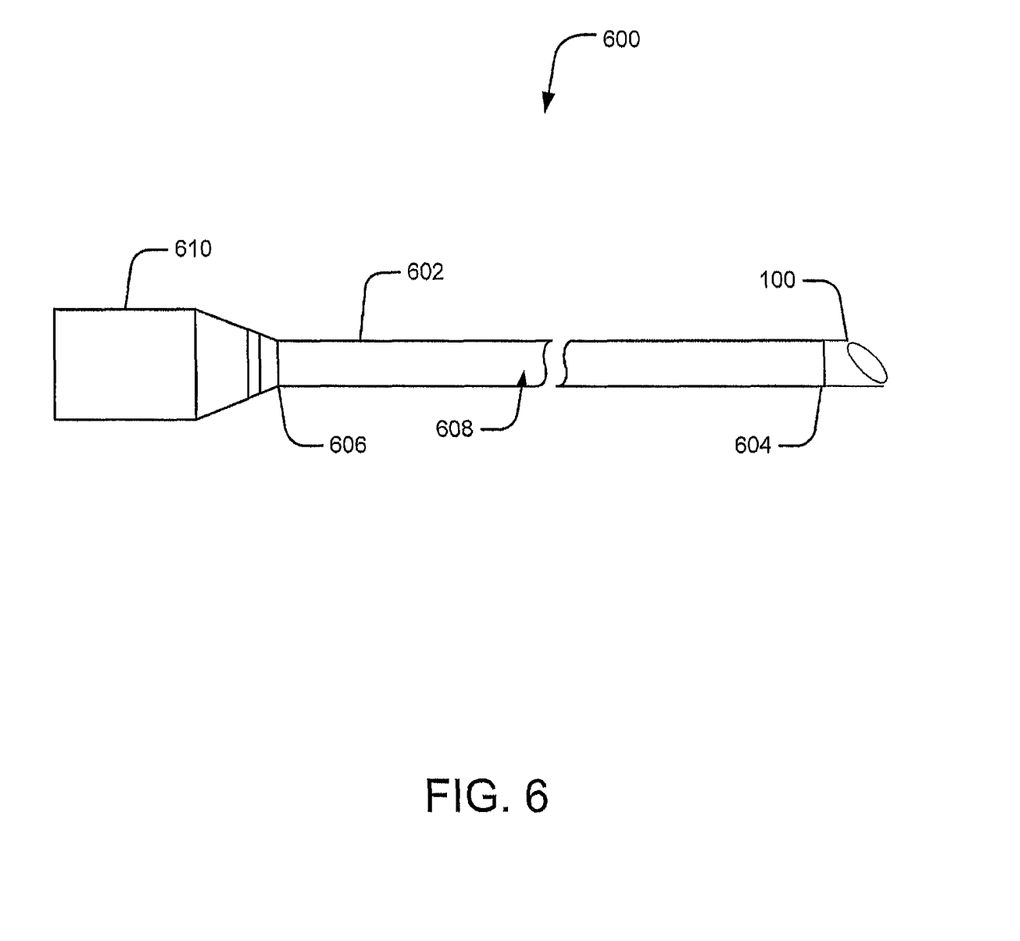
FIG. 6 illustrates an introduction sheath connected to the hood assembly of FIG. 1, according an embodiment of the present disclosure.

FIG. 6 is a perspective view of a medical assembly 600 for cutting and extracting an undesired mass through an incision or a natural body opening. The medical assembly 600 includes a sheath 602 with a distal end 604, a proximal end 606, joined by a lumen 608 extending therethrough. Proximal end 606 may be coupled to a handle 610, while distal end 604 is coupled to the hood assembly 100.

Sheath 602 may be an endoscope or any other suitable introduction device or sheath adapted to be advanced into a body lumen. In the illustrated embodiment, sheath 602 may include one or more channels (not shown), through which, the operator may introduce one or more medical devices to extend out of the distal end 604 of sheath 602. For example, during a resectomy, the operator may introduce a suction device into one channel and a cutting device, such as, for example, a snare loop into another channel. Additionally, from time to time during the procedure, the operator may insert a light source, a camera, an injector, or a morcellator within the one or more channels. Sheath 602 may be any known endoscopic device used for colonoscopy, resectoscopy, cholangioscopy, or mucosal resection, and thus, this device will not be discussed in greater detail.

The sheath 602 and the hood assembly 100 may be designed to impose minimum risk to the surrounding tissues while in use. To this end, the proximal or distal ends of these components may include geometrical structures, such as rounded or beveled terminal ends or faces, to reduce trauma and irritation to surrounding tissues. Further, the outer surface of the hood assembly 100 and sheath 602 may include any suitable coating or covering. For example, the outer surface may include a layer of lubricous material to facilitate insertion through a body lumen or surgical insertion. To inhibit bacterial growth in the body cavity, medical assembly 600 may be coated with an antibacterial coating.

To effectively maneuver the sheath 602 within a body cavity, the operator should know the exact location of the sheath in the cavity at all times. To this end, one or more portions of medical assembly 600 may be radiopaque, produced by inclusion of material such as barium sulfate in plastic material or one or more metal portions, which provide sufficient radiopacity. Alternatively, the distal end of the sheath 602 or one or more portions hood assembly 100 may include a radiopaque marker or sono-reflective marker (not shown). These markings facilitate detection of a position and/or orientation of sheath 602 within the patient's body, and a surgeon, with the aid of suitable imaging equipment, may track the path followed by the device and avoid potential damage to sensitive tissues. In other embodiments, assembly 600 is designed to fit through a working channel of an endoscope or suitable introduction sheath. Alternatively, the assembly 600 may be delivered adjacent to or over the endoscopic device.

The proximal end 606 of sheath 602 can be coupled to handle 610 for gripping/actuation by an operator such as a surgeon, while the distal end 604 remains open for medical devices to extend out. The handle 610 can be attached to sheath 602 by, for example, welding, use of an adhesive, or integrally forming with sheath 602.

Handle 610 may include one or more ports (not shown) to introduce medical devices into the working channels of the sheath 602. In some embodiments, suction source or irrigation feeds may be attached to a port for generating a suction force at the distal end of sheath 602, or deliver irrigation fluid to the desired location within a patient's body, respectively. Handle 610 may include ability to steer the distal end of the assembly 600. Further, the handle portion may include an actuating mechanism to actuate one or more medical devices at the distal end of the sheath. For example, the handle may include an actuating mechanism to maneuver and/or actuate the cutting tool 116. Similarly, it may include a mechanism to power on or off a suction device attached to its working channel. In addition, the handle may also include a plug for connection to an electrosurgical generator.

Hood assembly 100 may be coupled to the distal end of the sheath 602. In one embodiment, the hood assembly 100 may be detachably attached to the distal end of the sheath 602 using any known coupling technique such as snap-fitting, luer-lock, screw threading, etc. Before inserting the sheath 602 within a patient's body, the hood assembly 100 may be securely fixed thereto. Alternatively, the hood assembly 100 may be permanently coupled to the distal end of the sheath 602. Techniques such as gluing, welding, or sealing may be used.

Further, a swivel mechanism may be introduced between the sheath 602 and the hood assembly 100, such that the hood assembly 100 may easily articulate to make a greater surface contact with the target tissue. The handle 610 or proximal end of the sheath may include mechanism to rotate the hood assembly 100, as desired. Any suitable swivel mechanism may be used without departing from the scope of the present disclosure.

In addition, hood assembly 100 is connected to the sheath 602 such that the tail section 122 of the track 114 aligns with at least one of the working channels of the sheath 602. Effectively, the working channel of the sheath 602 may become an extension of the tail of the track 114. This may allow the cutting tool 116 to advance from the proximal end of the sheath 602 up to the distal end of the track 114.

Exemplary Resection Method

Figure 7A:
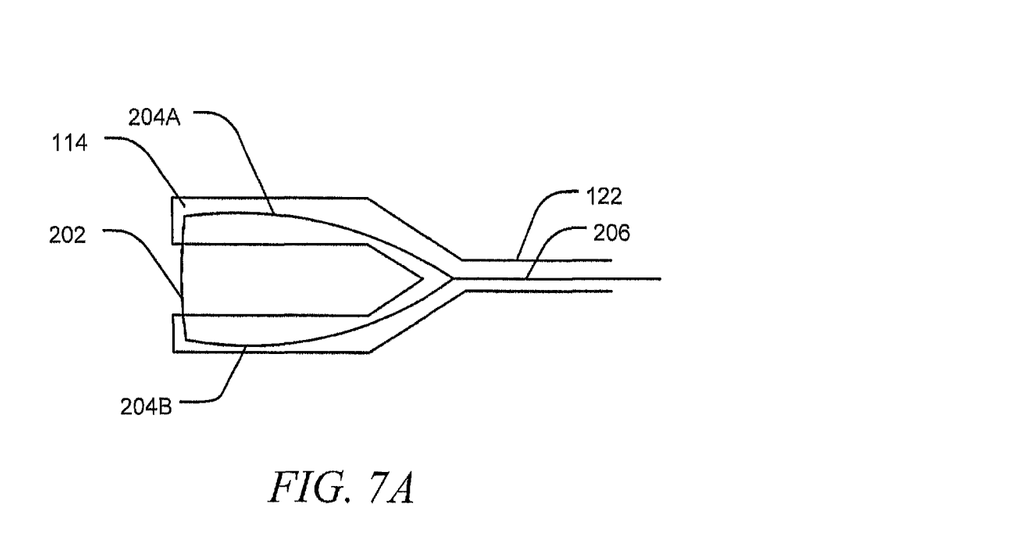
FIGS. 7A and 7B illustrate actuation of a cutting device used in conjunction with the introduction sheath and hood assembly of FIG. 6.
Figure 7B:
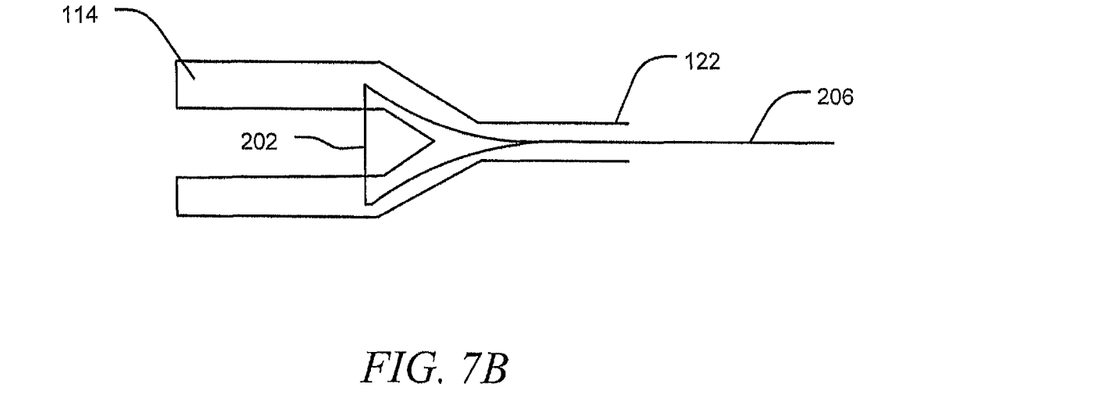

FIGS. 7A and 7B illustrate a method for resecting lesions, polyps or other tissue from a patient's body. Either a percutaneous incision is made to access the desired body part, or the assembly 600 may be inserted through a natural opening, such as the mouth or anus.

The assembly 600 may be directed towards targeted tissue. A steering mechanism may be incorporated in assembly 600 (with controls in the handle) to guide and urge the device within a body cavity such that the opening 108 of the hood assembly 100 is positioned adjacent the target tissue. A light source and a camera (not shown) may be inserted in the sheath's lumen to direct assembly 600 to identify the targeted tissue. Various identification techniques may be employed. For example, a biomarker or dye may be applied around the target body part. Cancerous lesions emit a different wavelength when light falls on them, allowing operators to easily detect them.

As discussed, the hood assembly 100 is configured to adjust the depth of its cavity 110. In one embodiment of the present disclosure, the position of the grate 112 may be adjusted to vary the volume of hood's cavity 110. Alternatively, if the grate 112 is fixed to the hood assembly 100, various depth adjustable mechanism may be employed. For example, a limiting member may be slidably introduced within the hood assembly from the proximal end. In some embodiments, the hood assembly 100 may be retracted relative to sheath 602 to control the cavity depth provided by the hood assembly 100.

In one embodiment, the cutting tool 116 including the cutting wire 202 may be pre-positioned under the distal lip 107 of opening 108. Here, the cutting tool 116 may be extended out to position over the target tissue as required. Alternatively, the cutting tool 116 may be introduced towards the hood assembly 100, once the opening 108 of hood assembly 100 is positioned over the target tissue. To this end, the tool 116 may be introduced through a channel of the sheath 602, extending up to the hood assembly 100. The cutting tool 116 traverses on the Y-shaped track 114 to advance towards the opening 108. The flexible material of the cutting tool 116 assists in sliding along the contours of the track 114. The tool 116 advances until the cutting wire 202 extends beyond the opening 108 i.e., under distal lip 107. Further, the junction point of the arms 202A, 202B acts as a stop to prevent over extension of the cutting tool 116. Once completely extended, the cutting tool 116 assumes its Y-shaped structure aligning with the Y-shaped track 114, as shown in FIG. 7A. The cutting tool 116 rests along the opening 108 on the track 114. Here, the cutting tool 116 including the cutting wire 202 may span the width of opening 108. In some embodiments, the cutting tool 116 may be positioned on the track 114 before inserting the medical assembly 600 within the body cavity.

Subsequently, a grasping device, such as suction pump, graspers, forceps, pincers, or any other such medical device that can draw the target tissue into the hood's cavity 110, is activated. In an embodiment of the present disclosure, a suction device, connected to a working channel of the sheath 602, introduces suction force that draws the tissue into the hood assembly 100. If the tissue is too flat along the surrounding tissue, the tissue may be injected with a saline solution to create a buffer layer, e.g., a bleb, which raises the target tissue off the surrounding tissue. Subsequently, suction of the target tissue within the hood assembly 100 may be easily accomplished.

In some embodiments, once the target tissue is completely drawn into the hood assembly 100, the cutting tool 116 may be activated. For example, suitable electrical energy may be provided to actuate the electrocautery wire. The proximal end of the actuation member 206 may include controls to actuate the cutting wire 202. Alternatively, proximal end of the sheath 602 or the handle 610 may be connected to an actuation source that supplies required electrical energy to the actuation member through conductive wires. The actuation member 202 subsequently actuates the cutting wire. In other embodiments, the cutting wire 202 may lie within one of the arms 104A, 104B during insertion and using controls available on handle, proximal end of the sheath 602 or the proximal end of the actuation member 206, the cutting wire 202 is exposed and held across the distal tip of the arms 104A, 104B, as shown in FIG. 1A.

Subsequently, the target tissue is resected by retrieving the cutting tool 116 proximally. As the cutting tool 116 is pulled proximally, the actuation member 206 traverses proximally on the tail portion 122. Subsequently, the proximal ends of the arms 104A, 104B converge in the tail section 122 of the Y-shaped track 114, as shown in FIG. 7B. The stops 124, positioned towards the proximal edge of the opening 108, limits the proximal movement of the cutting tool 116. The stops 124 are positioned such that the cutting wire 202 at least extends across the entire opening 108, ensuring complete resection of the tissue drawn into the hood assembly 100. Further, the stops 124 prevent hood assembly 100 from damage by avoiding the exposure of the cutting wire 202 to the hood assembly's surface.

Pulling the cutting tool 116 draws the cutting wire 202 across the opening 108 of the hood assembly 100 with sufficient potential force, resulting in resecting the tissue. For electrocautery tool, this potential force combined with the electrical activation of the cutting wire provides convenient tissue resection. In addition, the cutting wire 202 may be pulled under the lip 107, which may ensure complete cutting of the drawn tissue.

As the cutting tool is retrieved proximally, the resected tissue may move along with the cutting tool 202 and be collected in the opening 126. The resected mass may be removed from the body by a number of known mechanism. For example, the assembly 600 may extract the tissue or morcellate it and then extract it. For extraction, any retrieval device known now or later may be employed. In one embodiment, the tissue may be extracted with the help of suction force applied at the proximal end of the resection device 600. In another embodiment, a basket, a grasper, or pincers may be used. If the resected tissue is too large to fit in a working channel or be grasped in the retrieval device, it may be morcellated prior to extraction. A morcellator (not shown) may be introduced through a working channel of the sheath 602 for breaking the tissue into smaller pieces. Subsequently, any know retrieval device may extract the pieces.

In some embodiments, the resected mass may be reduced in size using laser, or a suitable heat sources that vaporize the mass, eliminating the need to pull out the mass from the body.

In some embodiments of the present disclosure, the tissue size may be greater than the opening 108 of the hood assembly 100. This situation may require subsequent dissection by assembly 600. To this end, a resection device having at least one straight side or edge of the opening 108 may be utilized such as the hood assembly 100 or hood assembly 400. For example, the hood assembly 100 may remove a rectangular shaped tissue section. Subsequently, the assembly 600 may be repositioned such that one of the straight edges of the hood assembly 100 may be aligned with one of the straight edges of the removed section. The tissue cutting process discussed above may be repeated to remove another rectangular portion of the tissue, allowing for subsequent cuts to be tessellated next to one another. Adjacent sections may be continually removed without leaving behind islands of tissue.

It should be understood that the resected tissue shape varies based on the configuration of opening 108. Accordingly, the shape of the resected portion may be square, rhombic, octagon, triangular, etc., so that at least one portion of one edge of the opening 108 is straight.

Embodiments of the present disclosure may be used in any medical or non-medical procedure, including any medical procedure where appropriate resection of an undesired body tissue is required. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A tissue resection hood, comprising:
   a distal end portion having an opening, wherein the opening is transverse to a longitudinal axis of the tissue resection hood, and wherein the opening includes at least one straight edge;
   a track that extends around a perimeter of the opening;
   a proximal end portion;
   a cavity defined between the proximal and distal end portions, wherein the proximal end portion defines an opening configured to couple to a distal end of a sheath;
   a cutting member configured to traverse the opening in the distal end portion, wherein the cutting member extends along the track around the perimeter of the opening when in a first configuration; and
   a mechanism configured to control an amount of tissue received in the cavity;
   wherein the tissue resection hood is coupled to the distal end of the sheath, and wherein the sheath has a proximal end and a lumen extending between the proximal end and the distal end.

2. The tissue resection hood of claim 1, wherein the mechanism controls a dimension of the cavity.

3. The tissue resection hood of claim 1, wherein the mechanism is an adjustable suction applied to the cavity.

4. The tissue resection hood of claim 1, wherein the mechanism is an adjustable structure disposed in the cavity.

5. The tissue resection hood of claim 1, wherein the mechanism is at least one of inflatable and mechanically expandable.

6. The tissue resection hood of claim 1, wherein the cutting member is configured to traverse the opening in the distal end portion from a distal end to a proximal end.

7. The tissue resection hood of claim 1, wherein a proximal end of the cavity includes stops configured to abut the cutting member.

8. A medical device comprising:
   a sheath having a proximal end, a distal end, and a lumen extending therebetween; and
   a hood coupled to a distal portion of the sheath, the hood comprising:
      a distal end portion having an opening, wherein the opening includes at least one straight edge;
      a track that extends around a perimeter of the opening;
      a proximal end portion;
      a cavity defined between the proximal and distal end portions, wherein the proximal end portion defines an opening configured to couple to the distal end of the sheath;
      a cutting member configured to traverse the opening in the distal end portion, wherein the cutting member extends along the track around the perimeter of the opening when in a first configuration; and
      a mechanism configured to adjust an amount of tissue received in the cavity.

9. The medical device of claim 8, wherein the mechanism controls a dimension of the cavity.

10. The medical device of claim 8, wherein the mechanism is an adjustable suction applied to the cavity.

11. The medical device of claim 8, wherein the mechanism is an adjustable structure disposed in cavity.

12. The medical device of claim 8, wherein the mechanism is configured to move relative to the opening.

13. The medical device of claim 8, wherein the mechanism is inflatable.

14. The medical device of claim 8, wherein the cutting member is configured to traverse the opening from a distal end to a proximal end when transitioning from the first configuration to a second configuration in which the cutting member does not extend around the perimeter of the opening.

15. A method for resecting target tissue from a body, the method comprising:
   advancing a medical device within a body lumen towards the target tissue, the medical device comprising:
      a sheath having a proximal end, a distal end, and a lumen extending therebetween,
      a hood coupled to a distal portion of the sheath, the hood comprising a cavity having an opening that includes at least one straight edge, a track that extends around a perimeter of the opening, and a proximal end portion defining an opening configured to couple to the distal end of the sheath, wherein the cavity is defined between the proximal end portion and the distal end, and
      a cutting member, wherein the cutting member extends along the track around the perimeter of the opening when in a first configuration;
   receiving the target tissue within the cavity; and
   activating the cutting member to transition the cutting member from the first configuration to a second configuration by moving the cutting member proximally relative to the opening so that the cutting member traverses the opening.

16. The method of claim 15, further comprising controlling an amount of target tissue received in the cavity by adjusting a position of a mechanism relative to the opening.

17. The method of claim 15, further comprising transitioning the cutting member from the second configuration to the first configuration before receiving the target tissue within the cavity.

* * * * *